United States Patent
Kofman

(10) Patent No.: US 10,257,602 B2
(45) Date of Patent: Apr. 9, 2019

(54) EARBUD INSERTION SENSING METHOD WITH INFRARED TECHNOLOGY

(71) Applicant: BOSE CORPORATION, Framingham, MA (US)

(72) Inventor: Igor Kofman, Weston, MA (US)

(73) Assignee: BOSE CORPORATION, Framingham, MA (US)

( * ) Notice: Subject to any disclaimer, the term of this patent is extended or adjusted under 35 U.S.C. 154(b) by 0 days.

(21) Appl. No.: 15/670,115

(22) Filed: Aug. 7, 2017

(65) Prior Publication Data

US 2019/0045291 A1 Feb. 7, 2019

(51) Int. Cl.
H04R 1/10 (2006.01)
A61B 5/00 (2006.01)

(52) U.S. Cl.
CPC ......... *H04R 1/1016* (2013.01); *A61B 5/0075* (2013.01); *H04R 1/105* (2013.01); *H04R 1/1091* (2013.01)

(58) Field of Classification Search
CPC ...... H04R 1/10; H04R 1/1016; H04R 1/1041; H04R 1/105
USPC .................................. 381/328, 74, 380, 384
See application file for complete search history.

(56) References Cited

U.S. PATENT DOCUMENTS

| | | | |
|---|---|---|---|
| 7,010,332 B1 | 3/2006 | Irvin et al. | |
| 7,212,835 B2 | 5/2007 | Mantyjarvi et al. | |
| 7,406,179 B2 | 7/2008 | Ryan | |
| 7,769,353 B2 | 8/2010 | Dietrich et al. | |
| 7,805,171 B2 | 9/2010 | Alameh et al. | |
| 7,930,007 B2 | 4/2011 | Andreasson | |
| 7,945,297 B2 | 5/2011 | Philipp | |
| 8,006,002 B2 | 8/2011 | Kalayjian et al. | |
| 8,045,727 B2 | 10/2011 | Philipp | |
| 8,238,567 B2 | 8/2012 | Burge et al. | |
| 8,259,984 B2 | 9/2012 | van der Bilt | |
| 8,315,406 B2 | 11/2012 | Kon | |
| 8,315,876 B2 | 11/2012 | Reuss | |
| 8,335,312 B2 | 12/2012 | Gerhardt et al. | |
| 8,428,053 B2 | 4/2013 | Kannappan | |
| 8,498,439 B2 | 7/2013 | Bae et al. | |
| 8,538,009 B2 | 9/2013 | Gerhardt et al. | |
| 8,559,621 B2 | 10/2013 | Gerhardt et al. | |
| 8,630,425 B2 | 1/2014 | Chang et al. | |
| 8,647,270 B2 | 2/2014 | LeBoeuf et al. | |
| 8,686,924 B2 | 4/2014 | Braun et al. | |
| 8,699,719 B2 | 4/2014 | Johnson, Jr. et al. | |

(Continued)

FOREIGN PATENT DOCUMENTS

CN 202721822 U 2/2013
CN 102761816 B 9/2014

(Continued)

OTHER PUBLICATIONS

International Search Report and Written Opinion from corresponding International Application No. PCT/US2018/044937 dated Oct. 23, 2018.

*Primary Examiner* — Katherine A Faley
(74) *Attorney, Agent, or Firm* — Lando & Anastasi, LLP

(57) ABSTRACT

An earbud includes an infrared light transmitter, an infrared light detector, and a controller configured to provide an indication of insertion of the earbud into an ear of a user responsive to detection of a pattern of signals from the transmitter at the detector.

21 Claims, 13 Drawing Sheets

(56) References Cited

U.S. PATENT DOCUMENTS

| | | | |
|---|---|---|---|
| 8,705,784 B2 | 4/2014 | Haartsen et al. | |
| RE44,980 E | 7/2014 | Sargaison | |
| 8,798,042 B2 | 8/2014 | Kannappan | |
| 8,805,452 B2 | 8/2014 | Lee | |
| 8,831,242 B2 | 9/2014 | Brown et al. | |
| 8,907,867 B2 | 12/2014 | Wong et al. | |
| 8,954,177 B2 | 2/2015 | Sanders | |
| 9,081,572 B2 | 7/2015 | Philipp et al. | |
| 9,094,501 B2 | 7/2015 | Smailagic et al. | |
| 9,094,764 B2 | 7/2015 | Rosener | |
| 9,117,443 B2 | 8/2015 | Walsh | |
| 9,124,970 B2 | 9/2015 | Rabii et al. | |
| 9,232,308 B2 | 1/2016 | Murata et al. | |
| 9,280,239 B2 | 3/2016 | Rosener | |
| 9,286,742 B2 | 3/2016 | Rosener et al. | |
| 9,338,540 B2 | 5/2016 | Nicholson | |
| 9,344,792 B2 | 5/2016 | Rundle | |
| 9,442,523 B2 | 9/2016 | Lee et al. | |
| 9,479,860 B2 | 10/2016 | Kwatra et al. | |
| 9,486,823 B2 | 11/2016 | Andersen et al. | |
| 9,549,055 B2 | 1/2017 | Widell et al. | |
| 9,590,680 B1 | 3/2017 | Reuss et al. | |
| 9,648,409 B2 | 5/2017 | Puskarich | |
| 9,838,775 B2 | 12/2017 | Qian et al. | |
| 2004/0121796 A1* | 6/2004 | Peng | H04B 1/385 455/522 |
| 2005/0096111 A1* | 5/2005 | Beck | A63F 13/02 463/7 |
| 2007/0274530 A1* | 11/2007 | Buil | H04R 1/1041 381/74 |
| 2010/0207879 A1* | 8/2010 | Fadell | G01J 1/4204 345/156 |
| 2013/0131519 A1 | 5/2013 | LeBoeuf et al. | |
| 2014/0016803 A1* | 1/2014 | Puskarich | H04R 1/1041 381/309 |
| 2014/0064500 A1* | 3/2014 | Lee | H04R 1/1041 381/58 |
| 2015/0208933 A1* | 7/2015 | Satomi | A61B 5/02416 600/479 |
| 2017/0094389 A1 | 3/2017 | Saulsbury et al. | |
| 2017/0323630 A1* | 11/2017 | Stickney | G10K 11/1788 |

FOREIGN PATENT DOCUMENTS

| | | |
|---|---|---|
| CN | 103002373 B | 5/2015 |
| CN | 205071294 U | 3/2016 |
| CN | 205081948 U | 3/2016 |
| CN | 205305076 U | 6/2016 |
| EP | 2415276 A1 | 2/2012 |
| JP | 4737496 B2 | 8/2011 |
| WO | 2017019885 A1 | 2/2017 |

* cited by examiner

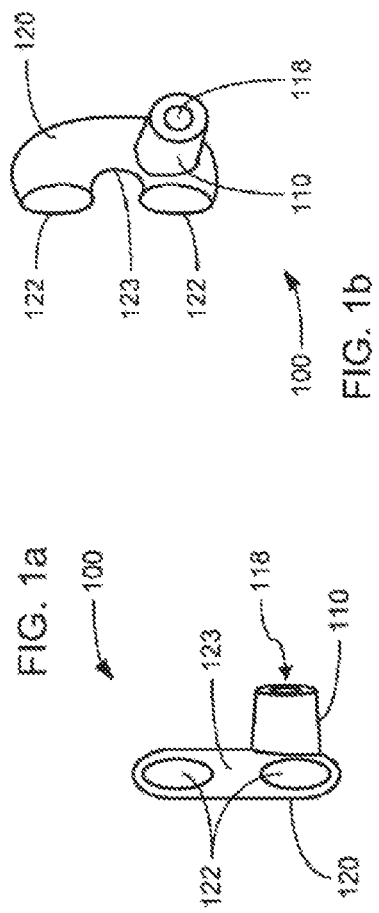

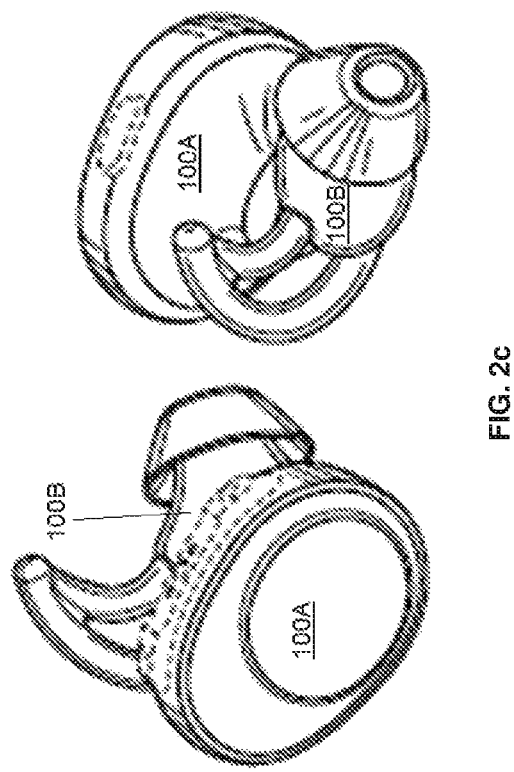

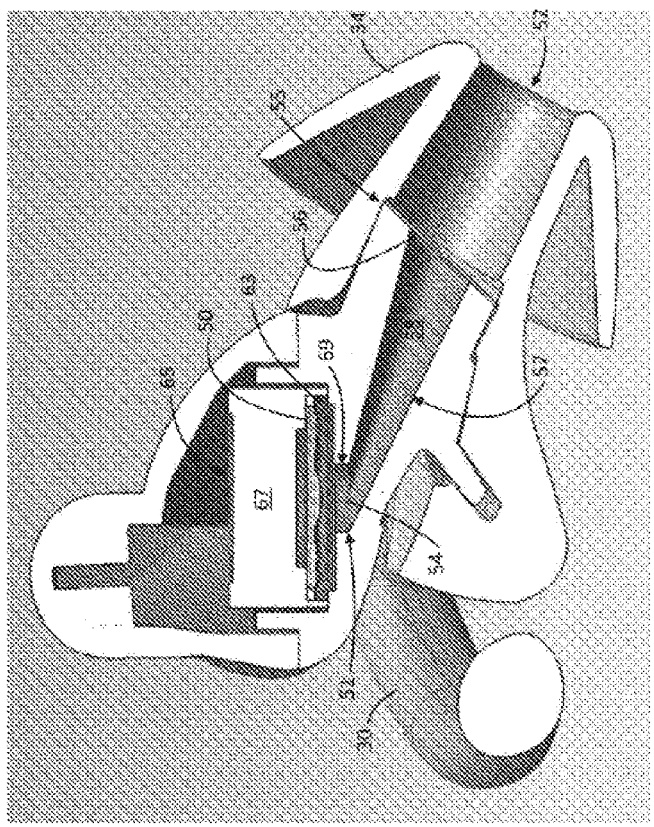

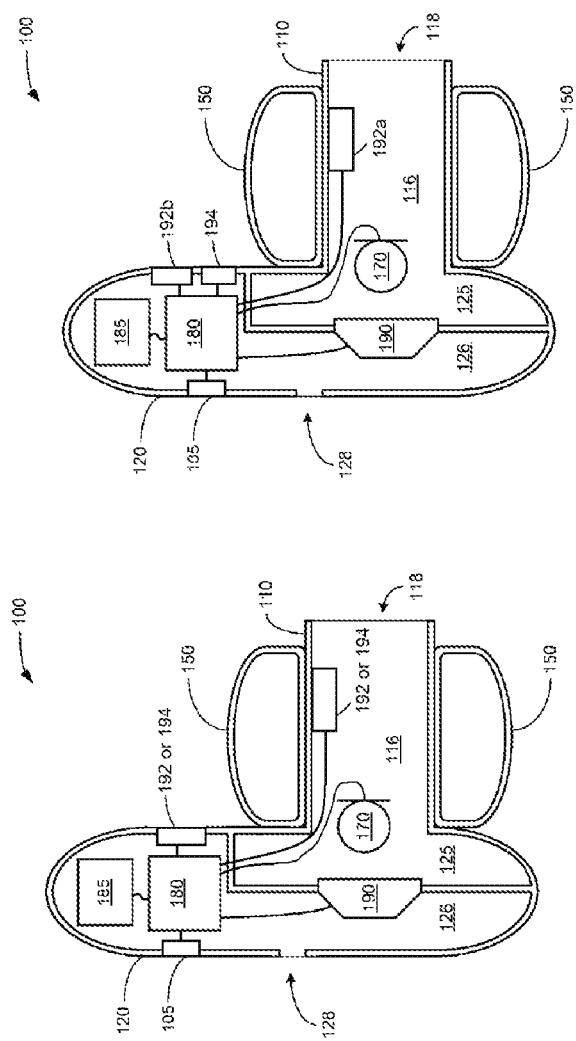

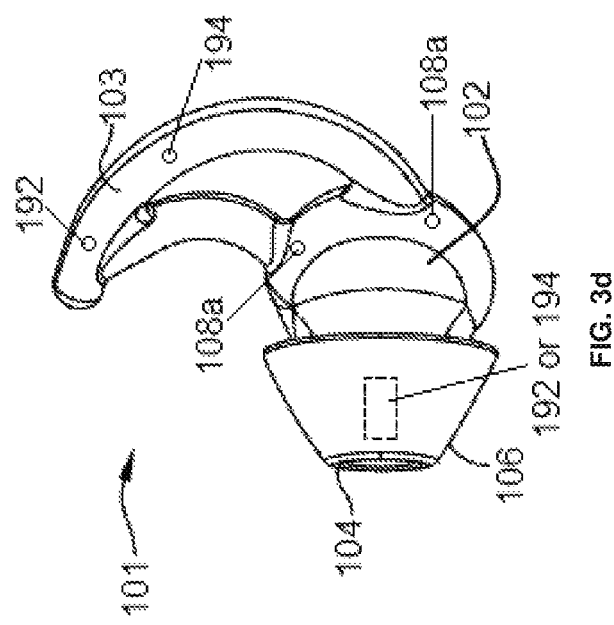

EARBUD INSERTION SENSING METHOD WITH INFRARED TECHNOLOGY

TECHNICAL FIELD

Aspects and implementations of the present disclosure are directed generally to earbuds and to systems and methods for extending the battery life or controlling audio playback of same.

BACKGROUND

Earbuds for use with consumer electronic devices, for example, audio players and two-way wireless communications devices (e.g., cell phones and personal data assistant devices incorporating cell phone capabilities) may be connected to an electronic device via a wired connection or wirelessly. Consumers generally prefer earbuds that are small and lightweight and comfortable to wear. Small and lightweight earbuds, however, can accommodate batteries of only a limited size and thus, a limited capacity. If a user accidentally powers on and sends audio to be played to an earbud while it is not in the ear of the user, or removes the earbud from the ear without first terminating rendering of audio by the earbud, battery life of the earbud may be unintentionally wasted. Further, it may be desirable to automatically control aspects of audio playback when the earbuds are placed in a user's ear or taken out of a user's ear.

SUMMARY

In accordance with an aspect of the present disclosure, there is provided an earbud comprising a concha portion, a canal portion, an infrared light transmitter disposed in one of the concha portion and the canal portion, an infrared light detector disposed in the other of the conch portion and the canal portion, and a controller configured to provide an indication of insertion of the earbud into an ear of a user responsive to detection of a pattern of signals from the transmitter at the detector.

In some implementations, the controller is further configured to cause the infrared light transmitter to emit a signal with a predetermined modulation and the infrared light detector is configured to detect signals exhibiting the predetermined modulation. The predetermined modulation may comprise a signal having a frequency outside of a band of frequencies between about 30 KHz and about 60 KHz.

In some implementations, the transmitter may be disposed in the canal portion, the detector may be disposed in the concha portion, and a second transmitter may be disposed in the concha portion.

In some implementations, the controller is configured to provide the indication of insertion of the earbud into the ear of the user responsive to a signal from the transmitter to the detector ceasing to be detected subsequent to the signal from the transmitter to the detector being detected. The controller may be configured to provide the indication of insertion of the earbud into the ear of the user responsive to a signal from the transmitter to the detector ceasing to be detected subsequent to the signal from the transmitter to the detector being detected, and a strength of a signal from the second transmitter to the detector increasing contemporaneous with or subsequent to the signal from the transmitter to the detector ceasing to be detected.

In some implementations, the controller is further configured to cause the earbud to transition from an active to an inactive state responsive to the controller failing to provide the indication of insertion of the earbud into the ear of the user after a set time after the earbud is placed into the active state. The controller may be further configured to cause the earbud to transition from an active to an inactive state responsive to the controller ceasing to provide the indication of insertion of the earbud into the ear of the user. The controller may be further configured to cause the transmitter to emit a locating signal responsive to the controller receiving a location query.

In accordance with another aspect, there is provided a method of reducing power consumption of an earbud. The method comprises determining whether the earbud is inserted into the ear of a user by monitoring a pattern of signals between an infrared light transmitter disposed in one of a concha portion or a canal portion of the earbud and an infrared light detector disposed in the other of the concha portion or canal portion of the earbud, and causing the earbud to transition from an active state to an inactive state responsive to determining that the earbud is not inserted in the ear of the user for more than a threshold amount of time.

The method may further comprise transmitting an infrared light signal from the transmitter with a specific modulation. The detector may be configured to detect infrared light signals having the specific modulation. The method may include transmitting the infrared signal from the transmitter with one of a specific pulse frequency or a specific pattern.

The method may further comprise determining that the earbud is inserted into the ear of the user responsive to a signal from the transmitter to the detector ceasing to be detected subsequent to the signal from the transmitter to the detector being detected. The method may further comprise determining that the earbud is inserted into the ear of the user responsive to a signal from the transmitter to the detector ceasing to be detected subsequent to the signal from the transmitter to the detector being detected, and a strength of a signal from a second transmitter to the detector increasing contemporaneous with or subsequent to the signal from the transmitter to the detector ceasing to be detected.

The method may further include emitting a locating signal from the transmitter responsive to the earbud receiving a location query.

The method may further include causing the earbud to transition from an active to an inactive state responsive to failing to determine that the earbud is inserted into the ear of the user after a set time after the earbud is placed into the active state. The method may further include causing the earbud to transition from an active to an inactive state responsive to determining that the earbud has transitioned from a state in which the earbud is inserted into the ear of the user to a state in which the earbud is not inserted into the ear of the user.

The method may further include communicating a signal between the earbud and an external device and, responsive to receiving the signal, one of handing off rendering of audio content from the earbud to the external device or handing off rendering of audio content from the external device to the earbud.

In accordance with another aspect, there is provided a method of detecting insertion of an earbud into an ear of a user. The method comprises detecting an infrared light signal transmitted from a transmitter disposed in one of a concha portion and a canal portion of the earbud at an infrared detector disposed in the other of the concha portion and the canal portion of the earbud, and detecting a termination of receipt of the infrared light signal at the infrared detector, the termination of the receipt of the infrared light signal being indicative of the earbud being inserted into the ear of the user. The method may further include detecting a second infrared signal transmitted from a second transmitter of the earbud at the infrared detector, the second infrared signal having an intensity above a set threshold value being indicative of the earbud being inserted into the ear of the user.

In accordance with another aspect, there is provided a pair of earbuds. The pair of earbuds comprises a first earbud comprising a first infrared light transmitter disposed in one of a concha portion and a canal portion of the first earbud and a first infrared light detector disposed in the other of the concha portion and the canal portion of the first earbud, a second earbud comprising a second infrared light transmitter disposed in one of a concha portion and a canal portion of the second earbud and a second infrared light detector disposed in the other of the concha portion and the canal portion of the second earbud, and a controller. The controller may be configured to cause the first transmitter to emit a signal with a first predetermined modulation, cause the first detector to be sensitive only to signals exhibiting the first predetermined modulation, cause the second transmitter to emit a signal with a second predetermined modulation, and cause the second detector to be sensitive only to signals exhibiting the second predetermined modulation, and provide an indication of insertion of the earbuds into ears of a user responsive to a failure to detect a pattern of signals from the transmitters at the detectors.

BRIEF DESCRIPTION OF DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings:

FIG. 1a is a perspective view of an example of in-ear audio device;

FIG. 1b is another perspective view of the example of the in-ear audio device of FIG. 1a;

FIG. 2c illustrates an example of a pair of wireless in-ear audio devices;

FIG. 2d is a perspective view in partial cross section of an example earpiece;

FIG. 3a is a partially cutaway view of the example of an in-ear audio device including an infrared transmitter and an infrared receiver;

FIG. 3b is a partially cutaway view of another example of an in-ear audio including two infrared transmitters and an infrared receiver;

FIG. 3d is another example of an eartip including infrared transmitters and receivers;

DETAILED DESCRIPTION

Figure 2A:
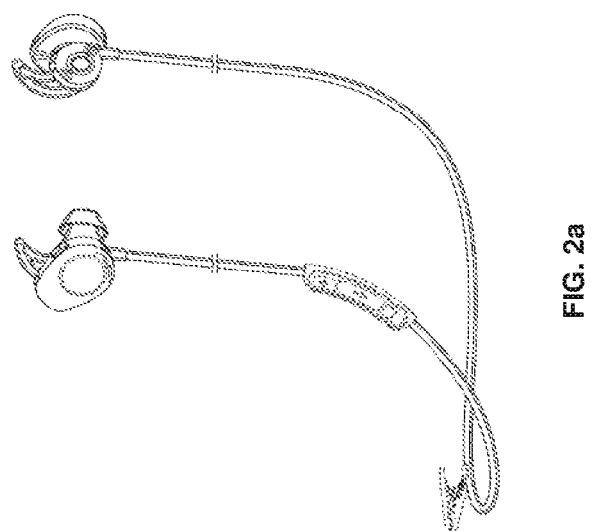
FIG. 2a is an isometric view of an in-ear audio device headset.

Aspects and implementations disclosed herein are not limited to the details of construction and the arrangement of components set forth in the following description or illustrated in the drawings. Aspects and implementations disclosed herein are capable of being practiced or of being carried out in various ways.

Aspects and implementations disclosed herein may be applicable to a wide variety of audio devices structured to be at least partly inserted into one or both ears of a user (e.g., so called "in-ear" audio devices or "intra-aural" audio devices), hereinafter referred to as "wireless earbuds" or simply "earbuds," and audio players. The examples discussed herein are directed primarily to earbuds, which may be wired or wireless, but the technology disclosed may also have application to over-the-ear earphones or other audio devices. It should be noted that although specific implementations of wireless earbuds primarily serving the purpose of acoustically outputting audio are presented with some degree of detail, such presentations of specific implementations are intended to facilitate understanding through provision of examples, and should not be taken as limiting either the scope of disclosure or the scope of claim coverage.

Aspects and implementations disclosed herein may be applicable to earbuds that either do or do not support two-way communications, and either do or do not support active noise reduction (ANR). For earbuds that do support either two-way communications or ANR, it is intended that what is disclosed and claimed herein is applicable to an earbud incorporating one or more microphones disposed on a portion of the earbud that remains outside an ear when in use (e.g., feedforward microphones), on a portion that is inserted into a portion of an ear when in use (e.g., feedback microphones), or disposed on both of such portions. Still other implementations of earbuds to which what is disclosed and what is claimed herein is applicable will be apparent to those skilled in the art.

Various implementations and examples disclosed herein may provide for increased battery life in wireless earbuds by automatically causing the earbuds to turn off or deactivate when not in use. Further, various implementations and examples disclosed herein may provide for automatic control of audio playback in wired or wireless earbuds, for example to play audio when in use and pause audio when not in use. In some implementations, wireless earbuds are provided with one or more sensors that may be used to determine if the earbuds are inserted into the ear of a user. If a user removes an earbud from the ear of the user without first terminating rendering of audio by the earbud, the earbud may detect that it has been removed from the ear of the user and may automatically pause audio, or terminate rendering of audio and turn the earbud off, optionally after a set time after being removed from the ear of the user. In some implementations, if a user turns on an earbud and does not insert it into the ear of the user within a set time period, the earbud may automatically shut off.

In various implementations earbuds may include one or more infrared (IR) transmitters and one or more IR receivers or detectors. An IR transmitter is used to transmit a specific pattern of IR light at intervals, based on a carrier frequency. The IR detector (or associated controller) filters or reacts to pulses of the carrier frequency exclusively, thus providing means of interference suppression (similar to IR remote controls however changed or adapted for in-ear detection). Further, the detector in each earbud in a set is able to register/discriminate a pattern from both earbuds.

In some implementations, an IR transmitter is placed inside an acoustic cavity or tube of an earbud and transmits IR light directly or via a light guide to the outside of the earbud (towards the ear canal when inserted). The acoustic cavity can be mirror plated to increase reflectance. The transmitter can be placed directly at the tube opening for maximum power.

The IR detector is placed to the outside of the acoustic cavity and is able to receive IR energy reflected from the ear or clothing when the cavity or tube portion of the earbud is not inserted into the ear of a user. Once the cavity or tube portion of the earbud is inserted into the ear of a user, the ear canal of the user obstructs or isolates the IR path between the IR transmitter and receiver. The system is intended to adapt and calibrate for a small amount of IR leakage that may be associated with poor insertion. Further, the IR receivers on the outside of each earbud can discriminate both transmitter patterns concurrently and thus inform a host system which earbud is removed. This provides flexibility with decisions as to which earbud carries the host system or controller.

To improve sensor discrimination an additional IR transmitter can be outfitted on the outside of each earbud. This additional IR transmitter generates a response similar to the one that is placed inside the earbud. When the earbud is in the inserted position the IR receiver reacts to an absolute and incremental reading from both IR transmitters. An insertion indicates no reading from one and a strong proximity reading from the other.

In some implementations, an IR transmitter is placed outside an acoustic cavity and is coupled via, for example, a Fresnel type lens for wide dispersion. The IR receiver or detector is placed inside an acoustic cavity or tube of the earbud and is intended to receive or discriminate transmitter signals as described above. Such transmitter placement has advantages where it can be more easily picked up by other receivers.

Sensors in earbuds as disclosed herein may be used to manage battery life as well as enable other user experience scenarios such as music, calls, virtual personal assistant, augmented reality, etc. For example, the sensor could provide a signal that indicates that a host system should route audio to an earbud inserted in to the ear of a user or signal a host system that the user is trying to gauge an aspect of their surroundings. The sensor could trigger a host system to use power modes like sleep and wake-up. The sensor could provide feedback on how well the earbud is seated in the ear canal of the user and adjust audio calibration accordingly.

The sensor output is specifically conducive to in-ear earbuds where it detects insertion inside the ear canal and not simply proximity to the ear. Further detecting insertion is advantageous as it significantly reduces the pulse rate needed for detection to further improve battery life. Proximity sensing methods must pulse frequently to continuously measure proximity gradient. An insertion detection method is an absolute threshold measurement that can be done infrequently.

For untethered earbuds, loss of one earbud is a potential issue. Implementations disclosed herein may address this concern. In some examples, if an earbud is separated or misplaced it may output a periodic pattern of infrared light that may be detected by other products having infrared detectors that could then provide a user with an indication of the location of the earbud. Alternatively, implementations of earbuds may include an "always listening microphone" that could trigger output of a pattern of infrared light in response to detecting a wake-up word or signal.

FIGS. 1a and 1b, taken together, provide two views of one implementation of an earbud 100. The examples illustrated in FIGS. 1a and 1b are schematic representations of one possible earbud configuration, but the ideas described herein apply to other configurations (for example, as shown in later figures), of earbuds including a "tube" or acoustic cavity in which to mount the transmitter/detector and a corresponding location outside of the earbud to mount a complimentary transmitter/detector. Earbud 100 includes a casing made up of at least a canal portion 110 meant to be positioned within at least an entrance of an ear canal of a user's ear and a concha portion 120 meant to be positioned within at least a portion of the concha of the user's ear. More specifically, and as depicted, the concha portion 120 has a curved shape to fit within the concha of a user's ear while accommodating the shape of the concha as defined by portions of the tragus, anti-tragus, and anti-helix of the pinna of the ear. This C-shaped configuration has a pair of extensions 122 and defines an inner periphery 123. The canal portion 110 has a generally tubular shape extending from where one end of the canal portion 110 is coupled to the concha portion 120 at a location coincident with where the entrance to the ear canal is typically located in relation to the portion of the concha defined by portions of the tragus and anti-tragus. An aperture 118 is formed in the other end of the canal portion 110 to enable sounds to be acoustically output by an acoustic driver (e.g., element 190 illustrated in FIG. 3a) positioned within the casing of the earbud 100 through the aperture 118 and into the ear canal when the earbud 100 is properly positioned in the ear of a user during operation.

The implementation of the earbuds 100 depicted in FIGS. 1a and 1b may be any of a variety of types of earbuds able to perform any of a variety of audio functions including, and not limited to, an in-ear earphone to acoustically output audio, an in-ear ANR device to provide a reduction in environmental noise sounds encountered by a user through the acoustic output of anti-noise sounds, and/or a two-way communications audio device employing detection of the user's speech sounds through bone conduction and/or a Eustachian tube connected to portions of the ear into which the in-ear audio device 100 is inserted. Further, it should be noted that although the concha portion 120 has been depicted and described as having a curved shape to fit within the concha, other implementations are possible having a somewhat differently shaped concha portion 120 that does not fill as much of the concha, or fills more of the concha.

The earbud 100 may receive audio through a wired or wireless coupling with another device. Accordingly, electrical and electronic components such as, but not limited to, a wireless receiver and/or transmitter, processor (optionally including ANR circuitry), battery, microphone, and acoustic driver may be included within the concha portion 120 and/or canal portion 110 of the earbud 100. Alternatively, such components may be included within a housing or casing coupled to the earbud.

Figure 2B:
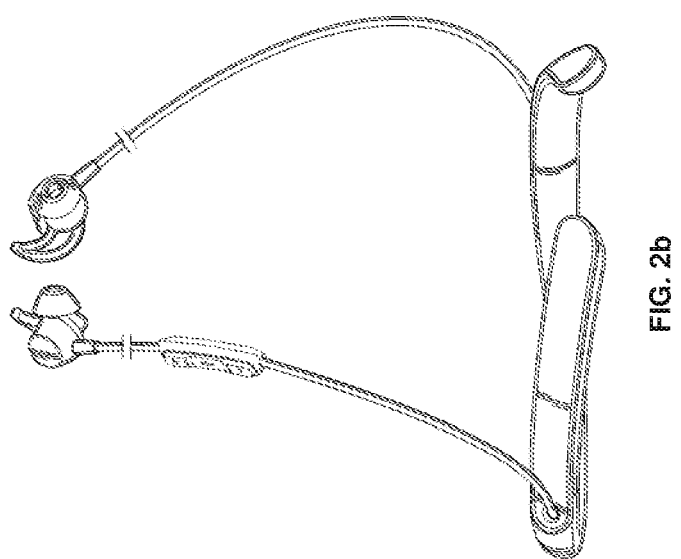
FIG. 2b is an isometric view of another in-ear audio device headset.

Examples of earbuds 100 disclosed herein are not limited to the form factors illustrated in FIGS. 1a and 1b. Other examples of form factors for earbuds are illustrated in FIGS. 2a-2d. The earbuds may be coupled by wiring as illustrated in FIGS. 2a and 2b to form headsets or may be mechanically separate, as illustrated in FIG. 2c. In various examples, the canal portion 110 or eartip may be separable from the concha portion 120 or may include a removable covering made of, for example, soft silicone to enhance comfort for a user. For example, in FIG. 2c, section 100A may include a rigid shell housing electronics such as an acoustic driver, wireless communication circuitry, battery, etc., while section 100B may be a removable eartip formed of a soft compliant material, for example, medical grade silicone.

Examples of earbuds 100 disclosed herein may have cross-sections similar to that illustrated in FIG. 2*d*. In the example illustrated in FIG. 2*d* an outer leg 30 may extend from the body of the earbud, similar to concha portion 120 in FIGS. 1*a* and 1*b* to retain the earbud in the ear of a user. A sealing structure 34 is provided to engage the entrance to the user's ear canal and defines an output aperture 52. An entrance cavity 69 to an acoustic nozzle 57 having an interior volume 58 may be provided proximal to an acoustic driver 50. Driver 50 is enclosed in a driver cavity 65 including a front cavity 63 having a first volume and a back cavity 67 having a second volume. An entrance cavity 69 may be formed in front of driver cavity 63 that transitions to an entrance aperture 51 of the nozzle 57. In the implementation shown in FIG. 2*d*, the output aperture 55 of nozzle 57 is significantly larger than the entrance aperture 51. A first acoustic mesh 54 is provided at the entrance aperture 51 of the acoustic nozzle proximate the acoustic driver 50, and a second acoustic mesh 56 is provided at the output aperture of the acoustic nozzle 57 distal from acoustic driver 50

FIGS. 3*a* and 3*b* show partially cut-away views of two different variants of an earbud 100 including sensor systems for determining if the earbud 100 is inserted into the ear of a user. It is to be understood that the form factor illustrated in FIGS. 3*a* and 3B is not limiting, and earbud 100 may alternatively have any of the form factors illustrated in FIGS. 1*a*-2*d* or other form factors known in the art. For example, in some implementations, the canal portion 110 may be angled relative to the concha portion rather than extending straight from a surface of the concha portion 120 as illustrated.

The sensor systems may include at least one IR transmitter 192 and at least one IR receiver 194 (also referred to herein as an IR detector). The at least one IR transmitter 192 may include one or more light emitting diodes and the at least one IR receiver 194 may include at least one IR sensitive photodiode. The eartip of the earbud 100 illustrated in FIGS. 3*a* and 3*b* is represented by element 150.

Both variants of the earbud 100 illustrated in FIGS. 3*a* and 3*b* may incorporate circuitry 180 and an acoustic driver 190 that is electrically coupled to the circuitry 180. Within the canal portion 110, a channel 116 is formed that extends from the aperture 118 through to an interior portion 125 of the concha portion 120. Within the concha portion 120, the interior portion 125 is separated by a wall structure and the acoustic driver 190 from another interior portion 126 in which the circuitry 180 is depicted as being disposed (though it should be noted that the circuitry 180 may be disposed in any of a variety of locations either within the casing of the earbud 100, or externally thereof). The earbuds 100 further include a battery 185 to power the various components and wireless communication circuitry built into the circuitry 180 or a separate circuit element (though this may also be located in a housing separate from earbud 100). The earbud 100 may also include a microphone 170 that is acoustically coupled to the channel 116 and/or the interior portion 125 and electrically coupled to the circuitry 180 for providing two-way communications through the earbud 100 or feedback-based ANR. Optionally, the earbud 100 may be activated or deactivated with a manually operable power switch 105.

Both of the variants of FIGS. 3*a* and 3*b* are depicted as having an aperture 128 formed between the interior portion 126 and the environment external to a user's ear. One or more of the apertures 128 may serve as acoustic ports to tune the frequency response of the acoustic driver 190 and/or may serve to enable equalization of air pressure between the ear canal and the external environment. The apertures 128 may have dimensions and/or other physical characteristics selected to acoustically couple portions within the casing of the earbud 100 to each other and/or to the external environment within a selected range of frequencies. Further, one or more damping elements (not shown) may be disposed within one or more of the apertures 128 to cooperate with characteristics of the acoustic driver 190 to alter frequency response.

Additionally or alternatively, one or more of the apertures 128 may be formed in the concha portion 120 (and/or in other portions of the casing) to provide a controlled acoustic leak between the ear canal and the external environmental for purposes of controlling the effects of variations in fit that may develop over time. As will be recognized by those skilled in the art, variations in the health or other aspects of the physical condition of a user can bring about minor alterations in the dimensions and/or shape of the ear canal over time such that the quality of the seal able to be formed with each insertion of the earbud 100 into the ear over time may degrade. Thus, in some implementations, the dimensions and/or other characteristics of one or more apertures 128 formed in the casing may be selected to aid in mitigating the effects of a slightly degraded quality of seal by providing a pre-existing leak of controlled characteristics that mitigates the acoustic effects of other leaks developing in the future in the seal between the casing of the earbud 100 and portions of the ear. For example, the dimensions of one or more apertures 128 may be selected to be large enough to provide a far greater coupling between the ear canal and the external environment than any other coupling through a leak in the seal that may develop at a later time.

The earbud variant depicted in FIG. 3*a* includes an IR transmitter 192 and an IR receiver 194. The IR transmitter 192 and IR receiver 194 may both be electrically coupled to the circuitry 180 and may receive drive signals (IR transmitter 192) from the circuitry 180 or send indications of detected IR light signals (IR receiver 194) to the circuitry 180. One of the IR transmitter 192 and IR receiver 194 is disposed within the canal portion 110 of the earbud 100 and the other of the IR transmitter 192 and IR receiver 194 is disposed on or in the concha portion 120 of the earbud 100. The specific location of the IR transmitter 192 or IR receiver 194 within the canal portion 110 of the earbud 100 shown is merely exemplary, and other locations within the canal portion may alternatively be used. The one of the IR transmitter 192 and IR receiver 194 disposed on the concha portion 120 of the earbud may be mounted flush with a surface of the concha portion 120 to enhance user comfort. When the IR transmitter 192 is disposed within the canal portion 110 of the earbud 100 it is positioned and arranged to transmit IR light out of the aperture 118 of the canal portion 110. When the IR transmitter 192 is disposed on the concha portion 120 of the earbud 100 it is positioned and arranged to transmit IR light in a direction toward where a surface of the ear of a user would be when the earbud 100 was inserted in the ear of the user, for example, generally parallel to or in the same general direction as the canal portion 110. When the earbud 100 is not inserted into the ear of a user, IR light transmitted by the IR transmitter 192 exits the aperture 118 of the canal portion 110 (for implementations where the IR transmitter is located in the canal portion 110) or is transmitted from the concha portion 120 (for implementations where the IR transmitter is located in or on the concha portion 120) and may reflect off of nearby objects and be detected by the IR receiver 194. When the earbud 100 is inserted into the ear of a user, the flesh of the ear canal and other portions of the ear of the user blocks light transmission between the IR transmitter 192 and IR receiver 194, thus providing an indication that the earbud 100 is inserted into the ear of the user. In some implementations, the IR transmitter 192 transmits pulses of IR light at a specific pulse frequency or pattern that may be recognized by circuitry associated with the IR receiver 194 and that may help the circuitry associated with the IR receiver 194 differentiate between IR light transmitted from the IR transmitter 192 and background IR light or IR light from another source. The two different earbuds 100 in a set of earbuds may include IR transmitters 192 that transmit IR light at different pulse frequencies or patterns. This may help prevent one earbud from confusing signals transmitted by its IR transmitter 192 with signals transmitted by the IR transmitter 192 of the other earbud.

The earbud variant depicted in FIG. 3b includes an IR receiver 194 and a pair of IR transmitters 192a and 192b. The IR transmitters 192a and 192b and IR receiver 194 may all be electrically coupled to the circuitry 180 and may receive drive signals (IR transmitters 192a and 192b) from the circuitry 180 or send indications of detected IR light signals (IR receiver 194) to the circuitry 180. The IR receiver 194 is located on or in the concha portion 120 of the earbud 100. A first IR transmitter 192a is located in the canal portion 110 of the earbud and a second IR transmitter 192b is disposed on or in the concha portion 120 of the earbud 100. The IR transmitter 192b and IR receiver 194 disposed on the concha portion 120 of the earbud may be mounted flush with a surface of the concha portion 120 to enhance user comfort.

The IR transmitter 192a disposed within the canal portion 110 of the earbud 100 is positioned and arranged to transmit IR light out of the aperture 118 of the canal portion 110. The IR transmitter 192b disposed on the concha portion 120 of the earbud 100 is positioned and arranged to transmit IR light in a direction toward where a surface of the ear of a user would be when the earbud 100 was inserted in the ear of the user, for example, generally parallel to or in the same general direction as the canal portion 110.

When the earbud 100 is not inserted into the ear of a user, IR light transmitted by the IR transmitter 192a disposed in the canal portion 110 exits the aperture 118 of the canal portion 110 and IR light transmitted by the IR transmitter 192b disposed on or in the concha portion 120 is transmitted from the concha portion 120. The IR light transmitted from the IR transmitters 192a and 192b may reflect off of nearby objects and be detected by the IR receiver 194.

When the earbud 100 is inserted into the ear of a user, the flesh of the ear canal and other portions of the ear of the user blocks light transmission between the IR transmitter 192a in the canal portion 110 and IR receiver 194. A strong reflected IR signal may be detected at the IR receiver 194 from the IR transmitter 192b disposed on the concha portion 120. The detection of the reflected signal from the IR transmitter 192b disposed on the concha portion 120 and blockage of the signal from the IR transmitter 192a in the canal portion 110 provides an indication that the earbud 100 is inserted into the ear of the user.

When inserting the earbud 100 into the ear of the user the IR light transmitted from the IR transmitter 192a disposed in the canal portion 110 is first blocked from the IR receiver 194. When the earbud 100 is more fully inserted into the ear of the user a signal from the IR transmitter 192b disposed on or in the concha portion 120 of the earbud reflected from the concha of the ear of the user increases in intensity until the earbud is fully inserted in the ear of the user. The pattern of IR light received at the IR receiver 194 may thus provide an indication of a degree to which the earbud is inserted into the ear of the user.

When a user removes the earbud 100 from the ear of the user, IR light transmitted by the IR transmitter 192b disposed on or in the concha portion 120 may be received again by the IR receiver prior to IR light transmitted from the IR transmitter 192a disposed in the canal portion 110.

In some implementations, the IR transmitters 192a and 192b transmit pulses of IR light at a specific pulse frequency or pattern that may be recognized by circuitry associated with the IR receiver 194 and that may help the circuitry associated with the IR receiver 194 differentiate between IR light transmitted from the IR transmitters 192a and 192b and background IR light or IR light from another source. The IR light transmitted by the different IR transmitters 192a and 192b may be transmitted with different pulse frequencies or patterns such that the circuitry associated with the IR receiver 194 may differentiate between IR light transmitted from the different IR transmitters 192a and 192b. The circuitry associated with the IR receiver 194 may determine which of the IR signals from which of the IR transmitters 192a and 192b is being blocked or sensed first and may thus determine if the earbud is being inserted or removed from the ear of the user. Further, similar to the variant illustrated in FIG. 3a, the two different earbuds 100 in a set of earbuds may include IR transmitters 192a and 192b that transmit IR light at different pulse frequencies or patterns. This may help prevent one earbud 100 from confusing signals transmitted by its IR transmitters 192a and 192b with signals transmitted by the IR transmitters 192a and 192b of the other earbud 100.

Figure 3C:
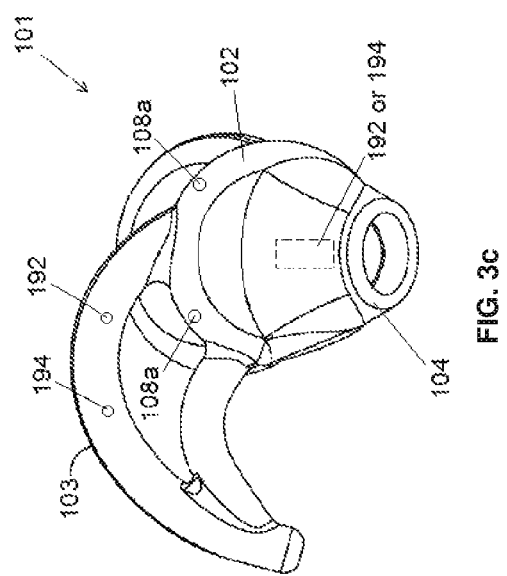
FIG. 3c is an example of an eartip including infrared transmitters and receivers.
Figure 3E:
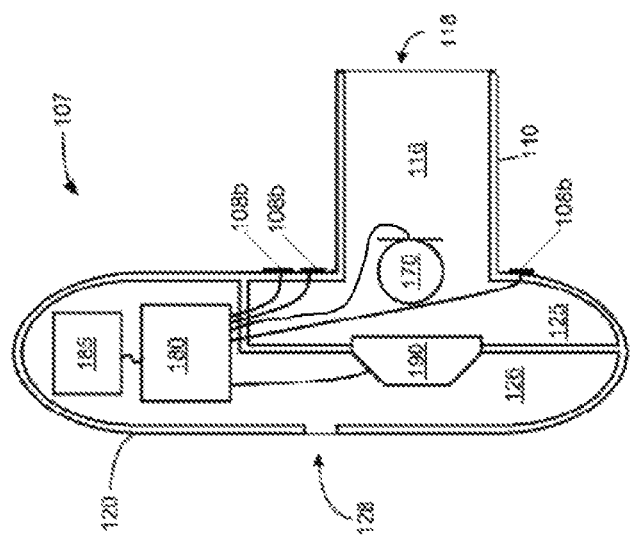
FIG. 3e is an example of an audio device that may be utilized with the eartips of FIG. 3c or 3d.

In the examples described so far, the one or more IR transmitters and one or more IR receivers have been shown as being disposed in the earbud itself, which may comprise a rigid shell housing, for example as illustrated in FIG. 2d. In further implementations one or more IR transmitters 192 and/or one or more IR receivers 194 may be incorporated into removable ear tips and/or retaining features for an earbud. Examples of removable ear tips are illustrated in FIGS. 3c and 3d, indicated generally at 101. These ear tips 101 have a configuration that includes a body 102 that rests in at least a part of the concha, a retaining leg 103 that rests against and applies pressure to the antihelix, and an outlet 104 that fits within at least an entrance in the ear canal. The ear tip 101 illustrated in FIG. 3d further includes a flexible flap 106 around the outlet. The construction and configuration of the removable ear tips 101 illustrated in FIGS. 3c and 3d are described in further detail in commonly owned U.S. Pat. Nos. 8,311,253 and 8,737,669, which are incorporated by reference in their entirety herein. In these ear tips, one or more IR transmitters 192 and/or one or more IR receivers 194 may be included in the retaining leg 103, body 102, outlet 104 and/or flap 106. Power and electrical communication may be provided to the one or more IR transmitters 192 and/or one or more IR receivers 194 in eartips 101 from a device 107, for example, as illustrated in FIG. 3e (illustrated as similar to the earbud of FIG. 3a with similar elements represented by similar reference numbers) upon which the eartips 101 are mounted during use via electrical couplings 108a on the eartips 101 and complimentary electrical couplings 108b on the device 107. Electrical couplings 108*a*, 108*b* may include inductive coils or may be configured to make physical contact with each other.

Figure 3F:
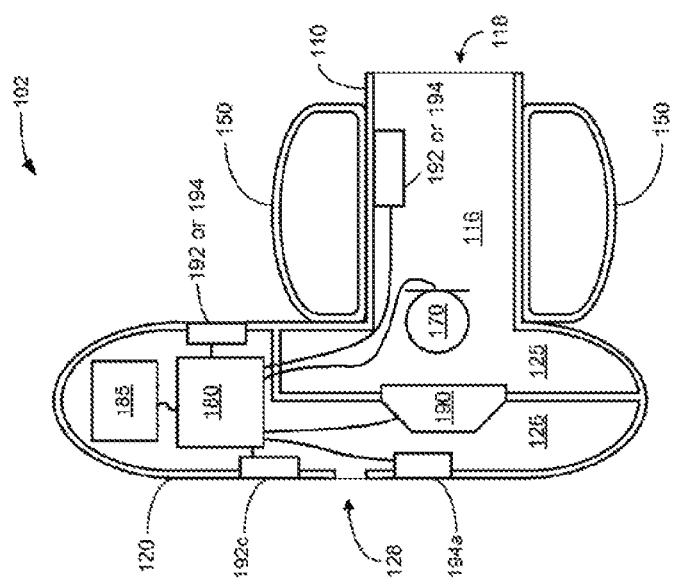
FIG. 3f is a partially cutaway view of another example of an in-ear audio including an outwardly facing infrared transmitter and infrared receiver.

In accordance with another implementation, an earbud may include an outwardly facing IR transmitter 192*c* and/or IR receiver 194*a* disposed on or in a portion of the concha portion 120 that faces away from the ear of a user when the earbud is inserted into the ear of a user. An example of an earbud 102 including such an outwardly facing IR transmitter 192*c* and IR receiver 194*a* is illustrated in FIG. 3*f*. In some implementations, the outwardly facing IR transmitter 192*c* and/or IR receiver 194*a* may provide for the earbud 102 to communicate with external devices. For example, if a user misplaces the earbud 102, a signal could be sent to the earbud 102 from an external device, for example, a cell phone, either using Wi-Fi or other radio frequencies or via an IR signal that would be detected by the IR receiver 194*a*. Responsive to receipt of the signal from the external device in the control circuitry, earbud 102 may cause the outwardly facing IR transmitter 192*c* to transmit a signal in a pattern or at a pulse frequency uniquely identifying the earbud 102. An external device, for example, a cell phone equipped with IR sensing capabilities may be used to search for the signal from the outwardly facing IR transmitter 192*c* and help a user located the misplaced earbud 102. Earbuds including IR transmitters disposed in other locations, for example, within a canal portion of the earbud may communicate with external devices in a similar manner.

Figure 4:
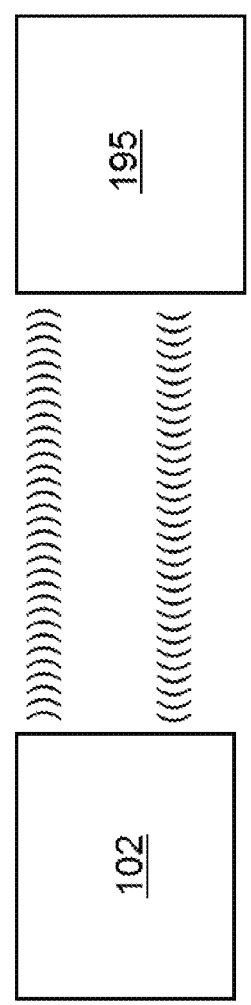
FIG. 4 illustrates infrared communications between an example of an in-ear audio device and an external device.

The earbud 102 may, in other examples, utilize the outwardly facing IR transmitter 192*c* and/or IR receiver 194*a* to communicate with or send or receive commands from other devices. In one example, if a user wearing the earbud 102 enters a room including a device equipped with an IR receiver or transmitter, the device may sense transmissions from the outwardly facing IR transmitter 192*c*, providing the device with an indication of the location of the user. The indication of the location of the user recorded by the device may assist in locating the earbud 102 if misplaced if the location of the user recorded by the device was a last known location at which a signal from the earbud 102 was detected. Illustration of communication between the earbud 102 and an external device 195 is illustrated in FIG. 4. If the external device 195 were an audio device, communications between the external device 195 and earbud 102 may provide for the earbud 102 to handoff rendering of audio content to the external device 195 or for the earbud to synchronize or receive a handoff of audio being rendered by the external device 195.

Figure 5:
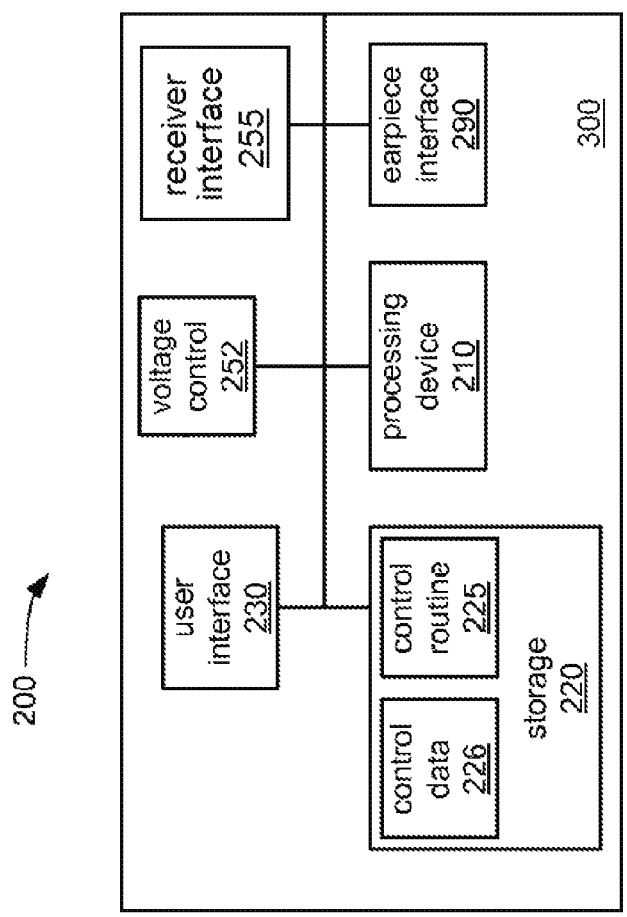
FIG. 5 is a block diagram of an example of a controller for an in-ear audio device.

FIG. 5 provides a block diagram of a controller 200 with which insertion of an earbud as disclosed herein within an ear of a user may be detected. The controller 200 may be included within the body of an earbud, for example, within circuitry 180. The controller may be formed on a circuit board 300. Each earbud in a pair of earbuds may include a controller 200, or a single controller 200 may control operation of both earbuds in a pair and may communicate via a wired or wireless connection between the two earbuds in the pair.

The controller 200 incorporates a voltage control 252 to controllably provide a voltage to one or more IR transmitters 192 disposed in the canal portion 110 and/or the concha portion 120 of the casing of an earbud 100 or in a removable eartip 101 of an earbud. The voltage control 252 may modulate the voltage sent to each IR transmitter 192 in an earbud or pair of earbuds so that each IR transmitter 192 emits an IR signal with a different pulse frequency or pattern. The pulse frequency or frequencies utilized may be outside a frequency range commonly used by other devices that may cause signal interference with examples of the earbuds disclosed herein, for example, infrared remote controls which typically operate at a frequency range of between about 30-60 KHz. In other implementations, however, the pulse frequency or frequencies utilized by the IR transmitter or transmitters of earbuds disclosed herein may be within the frequency range of between about 30-60 KHz.

The controller 200 also incorporates a user interface 230 which may wirelessly communicate with an external system, for example, a cell phone or computer, for receiving programming or providing recorded information, a storage 220 in which is stored a control routine 225, and a processing device 210 coupled to the storage 220 to access and execute a sequence of instructions of the control routine 225. The processing device 210 is also coupled to the voltage control 252 to operate the voltage control 252 to effect the application of a controlled voltage to the one or more of the IR transmitters 192 and is further coupled to the receiver interface 255 which receives signals from the one or more IR receivers 194 disposed in the canal portion 110 and/or the concha portion 120 of the casing of an earbud 100 or in a removable eartip 101 of an earbud. The controller 200 also incorporates at least an earpiece interface 290 to enable coupling of the controller 200 to the built-in microphone 170 and the acoustic driver 190 to be driven to acoustically output various test sounds that may be used to help calibrate the determination of insertion of earbuds in the ear of a user by the controller 200. In some implementations separate voltage controllers 252 are provided for each IR transmitter 192 in an earbud or pair of earbuds, and in other implementations, a single voltage controller 252 is used with each IR transmitter 192 in an earbud or pair of earbuds. Similarly, in some implementations separate receiver interfaces 255 are provided for each IR receiver 194 in an earbud or pair of earbuds, and in other implementations, a single receiver interface 255 is used with each IR receiver 194 in an earbud or pair of earbuds.

Figure 6:
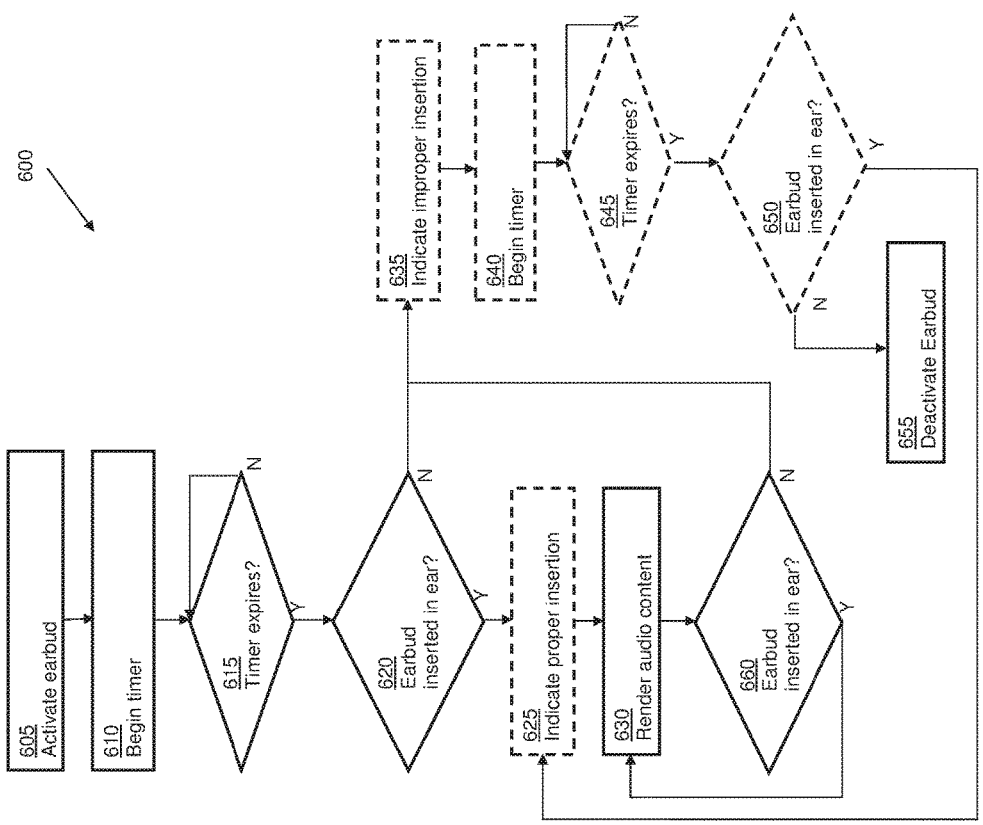
FIG. 6 is a flow chart of a method for using examples of in-ear audio devices disclosed herein.

An implementation of a method of operating an earbud 100 with an IR transmitter 192 and an IR receiver 194 as shown in FIG. 3*a* is illustrated in the flowchart of FIG. 6, indicated generally at 600. In act 605 a user activates the earbud. The user may activate the earbud by pressing a power switch. Additionally or alternatively, the earbud may include an accelerometer, for example, a microelectromechanical accelerometer built into the circuitry of the earbud that detects movement of the earbud and may activate the earbud when a user picks up the earbud. Activation of the earbud may cause a timer to begin counting down (acts 610, 615). Upon expiration of the timer (act 615) the earbud controller may determine whether a signal from the IR transmitter 192 is being received at the IR receiver 194 to determine if the earbud is inserted into the ear of the user (act 620). In some embodiments, the earbud controller determines that the earbud is inserted into the ear of the user if a signal from the IR transmitter 192 was first received at the IR receiver 194 (as the user brought the earbud towards the ear of the user) and then the signal ceased to be detected at the IR receiver 194 (as the canal portion of the earbud was inserted into the ear canal of the ear of the user). In some examples, the signal from the IR transmitter 192 need not be entirely blocked from the IR receiver 194 for the earbud controller to make the determination that the earbud is inserted into the ear of the user. A threshold amount of signal attenuation between IR transmitter 192 and IR receiver 194, for example, at least about 90% signal attenuation or at least about 75% signal attenuation may be set for determining if the earbud is inserted into the ear of the user.

If the earbud was determined to be properly inserted in the ear of the user in decision act 620, the earbud may optionally provide an indication of proper insertion being detected, for example, by emitting a click or a tone (act 625) and the earbud may begin to render audio content (act 630). In some embodiments, the earbud need not wait for the timer to expire but may continuously check for proper insertion of the earbud after the earbud is activated and may provide an indication of proper insertion being detected and begin to render audio any time prior to expiration of the timer.

If the earbud was not determined to be properly inserted in the ear of the user in decision act 620 or prior to expiration of the timer, the earbud may optionally provide an indication of improper insertion (act 635), for example, a pattern of clicks or a tone different from that used to provide an indication of proper insertion of the earbud in the ear of the user. The earbud may then begin and await expiration of a second timer (acts 640, 645) and if the earbud is not determined to be properly inserted in the ear of the user prior to or at the time of expiration of the second timer (act 650), the earbud controller may deactivate the earbud (act 655). If, however, in decision act 650 the earbud controller determines that the earbud is properly inserted into the ear of the user it may optionally provide an indication of proper insertion being detected, for example, by emitting a click or a tone (act 625) and the earbud may begin to render audio content (act 630).

Periodically, for example, at a rate of between about 1 second, 5 seconds, 10 seconds, 30 seconds, 1 minute or 5 minutes, the earbud may recheck if it is still inserted into the ear of the user (act 660). In addition, or alternatively, upon detection of an event, for example, detecting movement of the earbud via an accelerometer built into the earbud, the earbud may recheck if it is still inserted into the ear of the user (act 660). If the earbud is still inserted into the ear of the user the earbud may continue rendering audio content. If in decision act 660 the earbud controller determines that the earbud is not still inserted into the ear of the user, for example, by determining that the signal from the IR transmitter 192 was again received at the IR receiver 194, or by determining that the signal above a pre-set signal strength from the IR transmitter 192 was again received at the IR receiver 194, the method may proceed to act 635 and the earbud may provide the indication of improper insertion and be deactivated if not determined to be inserted into the ear of the user prior to expiration of the second timer (acts 640-655).

It is to be understood the method illustrated in FIG. 6 may also be applicable to earbuds having a pair of IR transmitters 192, for example, as in the earbud illustrated in FIG. 3b, and may also be applicable to implementations where one or more IR transmitters and/or one or more IR receivers are incorporated into removable ear tips, as in FIGS. 3c-3e. The method illustrated in FIG. 6, with modification as needed, may also be applicable to detecting proper insertion of both earbuds in a pair of earbuds. For example, in decision acts 620, 650, and 660, the earbud controller may make a determination if one or both of the earbuds in a pair of earbuds are properly inserted into the ear of a user, may cause audio content to be rendered through one or both earbuds in act 630, and may deactivate one or both earbuds in the pair in act 655.

Having thus described several aspects of at least one implementation, it is to be appreciated various alterations, modifications, and improvements will readily occur to those skilled in the art. Such alterations, modifications, and improvements are intended to be part of this disclosure, and are intended to be within the spirit and scope of the disclosure. The acts of methods disclosed herein may be performed in alternate orders than illustrated, and one or more acts may be omitted, substituted, or added. One or more features of any one example disclosed herein may be combined with or substituted for one or more features of any other example disclosed. Accordingly, the foregoing description and drawings are by way of example only.

The phraseology and terminology used herein is for the purpose of description and should not be regarded as limiting. As used herein, the term "plurality" refers to two or more items or components. As used herein, dimensions which are described as being "substantially similar" should be considered to be within about 25% of one another. The terms "comprising," "including," "carrying," "having," "containing," and "involving," whether in the written description or the claims and the like, are open-ended terms, i.e., to mean "including but not limited to." Thus, the use of such terms is meant to encompass the items listed thereafter, and equivalents thereof, as well as additional items. Only the transitional phrases "consisting of" and "consisting essentially of," are closed or semi-closed transitional phrases, respectively, with respect to the claims. Use of ordinal terms such as "first," "second," "third," and the like in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

What is claimed is:

1. An earbud comprising:
 a concha portion;
 a canal portion;
 a first infrared light transmitter disposed within a channel of the canal portion;
 a second infrared light transmitter disposed in the concha portion;
 an infrared light detector disposed in the concha portion; and
 a controller configured to cause the first infrared light transmitter to transmit pulses of infrared light in a first pattern, to cause the second infrared light transmitter to transmit pulses of infrared light in a second pattern different from the first pattern, and to provide an indication of insertion of the earbud into an ear of a user responsive to the pulses of infrared light having the first pattern ceasing to be detected by the infrared light detector and the pulses of infrared light having the second pattern being detected by the infrared light detector.

2. The earbud of claim 1, wherein the controller is further configured to cause the infrared light detector to differentiate between the pulses of infrared light transmitted from the first infrared light transmitter and the pulses of infrared light transmitted from the second infrared light transmitter.

3. The earbud of claim 2, wherein the first pattern and the second pattern comprise signals having frequencies outside of a band of frequencies between about 30 KHz and about 60 KHz.

4. The earbud of claim 1, wherein the controller is configured to provide the indication of insertion of the earbud into the ear of the user responsive to the pulses of infrared light transmitted by the first infrared light transmitter ceasing to be detected by the infrared light detector subsequent to the pulses of infrared light transmitted by the first infrared light transmitter being detected by the infrared light detector, and a strength of the pulses of infrared light transmitted by the second infrared light transmitter detected by the infrared detector increasing contemporaneous with or subsequent to the pulses of infrared light transmitted by the first infrared light transmitter ceasing to be detected by the infrared light detector.

5. The earbud of claim 1, wherein the controller is further configured to cause the earbud to transition from an active state to an inactive state responsive to the controller failing to provide the indication of insertion of the earbud into the ear of the user after a set time after the earbud is placed into the active state.

6. The earbud of claim 1, wherein the controller is further configured to cause the earbud to transition from an active state to an inactive state responsive to the controller ceasing to provide the indication of insertion of the earbud into the ear of the user.

7. The earbud of claim 1, wherein the controller is further configured to cause an outwardly facing infrared light transmitter of the earbud to emit a locating signal responsive to the controller receiving a location query from an external device.

8. The earbud of claim 1, wherein the controller is further configured to cause the earbud to provide an audible indication of insertion of the earbud in the ear of the user responsive to the controller providing the indication of insertion of the earbud into the ear of the within a set time after the earbud is placed into an active state.

9. The earbud of claim 1, wherein the controller is further configured to cause the earbud to provide an audible indication of improper insertion of the earbud in the ear of the user responsive to the controller failing to provide the indication of insertion of the earbud into the ear of the user after a set time after the earbud is placed into an active state.

10. A method of reducing power consumption of an earbud, the method comprising:
   determining whether the earbud is inserted into the ear of a user by monitoring a pattern of signals between a first infrared light transmitter disposed within a channel of a canal portion of the earbud, a second infrared light transmitter disposed in a concha portion of the earbud, and an infrared light detector disposed in the concha portion of the earbud, the first infrared light transmitter transmitting a first infrared light signal having a first pattern, the second infrared light transmitter transmitting a second infrared light signal having a second pattern different from the first pattern; and
   causing the earbud to transition from an active state to an inactive state responsive to determining that the earbud is not inserted in the ear of the user for more than a threshold amount of time.

11. The method of claim 10, further comprising the detector differentiating between the first infrared light signal transmitted from the first infrared light transmitter and the second infrared light signal transmitted from the second infrared light transmitter.

12. The method of claim 10, comprising transmitting the first infrared signal from the first infrared light transmitter with a first specific pulse frequency and transmitting the second infrared signal from the second infrared light transmitter with a second specific pulse frequency.

13. The method of claim 10, further comprising determining that the earbud is inserted into the ear of the user responsive to the first infrared light signal from the first infrared light transmitter ceasing to be detected by the infrared light detector subsequent to the first infrared light signal from the first infrared light transmitter being detected by the infrared light detector.

14. The method of claim 10, further comprising determining that the earbud is inserted into the ear of the user responsive to the first infrared light signal from the first infrared light transmitter ceasing to be detected by the infrared light detector subsequent to the first infrared light signal from the first infrared light transmitter being detected by the infrared light detector, and a strength of the second infrared light signal from the second infrared light transmitter detected by the infrared light detector increasing contemporaneous with or subsequent to the first infrared light signal from the first infrared light transmitter ceasing to be detected by the infrared light detector.

15. The method of claim 10, further comprising emitting a locating signal from an outwardly facing infrared light transmitter disposed on the earbud responsive to the earbud receiving a location query from an external device.

16. The method of claim 10, further comprising causing the earbud to transition from the active to the inactive state responsive to failing to determine that the earbud is inserted into the ear of the user after a set time after the earbud is placed into the active state.

17. The method of claim 10, further comprising causing the earbud to transition from the active to the inactive state responsive to determining that the earbud has transitioned from a state in which the earbud is inserted into the ear of the user to a state in which the earbud is not inserted into the ear of the user.

18. The method of claim 10, further comprising communicating a signal between the earbud and an external device and, responsive to receiving the signal, one of handing off rendering of audio content from the earbud to the external device or handing off rendering of audio content from the external device to the earbud.

19. A method of detecting insertion of an earbud into an ear of a user, the method comprising:
   detecting a first infrared light signal transmitted from a first transmitter disposed in a channel of a canal portion of the earbud at an infrared detector disposed in a concha portion of the earbud;
   detecting a second infrared light signal transmitted from a second transmitter disposed in the concha portion of the earbud, the second infrared light signal having a different pattern than the first infrared light signal; and
   detecting a termination of receipt of the first infrared light signal at the infrared detector, the termination of the receipt of the first infrared light signal being indicative of the earbud being inserted into the ear of the user.

20. The method of claim 19, wherein detecting the second infrared light signal with an intensity above a set threshold value provides an indication to a controller of the earbud that the earbud is inserted into the ear of the user.

21. A pair of earbuds comprising:
   a first earbud comprising a first infrared light transmitter disposed in a concha portion of the first earbud, a second infrared light transmitter disposed in a channel of a canal portion of the first earbud, and a first infrared light detector disposed in the concha portion of the first earbud;
   a second earbud comprising a third infrared light transmitter disposed in a concha portion of the second earbud, a fourth infrared light transmitter disposed in a channel of a canal portion of the second earbud, and a second infrared light detector disposed in the concha portion of the second earbud; and a controller configured to:
- cause the first transmitter to emit a signal with a first predetermined modulation;
- cause the second transmitter to emit a signal with a second predetermined modulation, the second predetermined modulation being different in one of frequency or pattern from the first predetermined modulation;
- cause the third transmitter to emit a signal with a third predetermined modulation;
- cause the fourth transmitter to emit a signal with a fourth predetermined modulation, the fourth predetermined modulation being different in one of frequency or pattern from the third predetermined modulation;

and

- provide an indication of insertion of the earbuds into ears of a user responsive to the signals from the second and fourth transmitters ceasing to be detected at the detectors.

* * * * *